(12) United States Patent  
Tseng et al.

(10) Patent No.: US 8,891,844 B2  
(45) Date of Patent: Nov. 18, 2014

(54) TIME SYNCHRONIZATION CALIBRATION METHOD AND SYSTEM FOR IMAGE TAKING AND COORDINATE READING AND DELAY TIME CALCULATION METHOD THEREOF

(71) Applicant: National Central University, Jhongli (TW)

(72) Inventors: Ching-Shiow Tseng, Jhongli (TW); Alex Tse, Jhongli (TW); Chih-Ju Chang, Jhongli (TW)

(73) Assignee: National Central University, Jhongli, Taoyuan County (TW)

( * ) Notice: Subject to any disclaimer, the term of this patent is extended or adjusted under 35 U.S.C. 154(b) by 144 days.

(21) Appl. No.: 13/791,149

(22) Filed: Mar. 8, 2013

(65) Prior Publication Data

US 2014/0133730 A1 May 15, 2014

(30) Foreign Application Priority Data

Nov. 9, 2012 (TW) .............................. 101141837 A

(51) Int. Cl.  
*G06K 9/00* (2006.01)  
*G06K 9/32* (2006.01)

(52) U.S. Cl.  
CPC ...................................... *G06K 9/32* (2013.01)  
USPC .............. 382/128; 382/152; 702/33; 702/155

(58) Field of Classification Search  
CPC .. G06K 9/32; G06T 2207/30108; G01H 3/00; G01H 1/00; G07C 3/00; G01B 9/00; G01B 11/00  
USPC .............. 382/100, 128–132, 152; 702/33–56, 702/150, 155  
See application file for complete search history.

(56) References Cited

U.S. PATENT DOCUMENTS

| | | | | |
|---|---|---|---|---|
| 5,827,942 A | * | 10/1998 | Madsen et al. | 73/1.82 |
| 5,943,133 A | * | 8/1999 | Zeylikovich et al. | 356/496 |
| 6,167,295 A | * | 12/2000 | Cosman | 600/426 |
| 8,401,312 B2 | * | 3/2013 | Chertok et al. | 382/224 |
| 2010/0007740 A1 | * | 1/2010 | Greiffenhagen et al. | 348/169 |

* cited by examiner

*Primary Examiner* — Shefali Goradia  
(74) *Attorney, Agent, or Firm* — Juan Carlos A. Marquez; Bacon & Thomas PLLC

(57) ABSTRACT

A time synchronization calibration method and system for image taking and coordinate reading and a delay time calculation method thereof are disclosed. The time synchronization calibration method is as follows. Firstly, every time point, a calibrator coordinate, an operation target coordinate and an image thereof are obtained. The image similarity index of every image and the image of previous time point thereof is calculated. When the image similarity index is lower than a preset similarity index, a reading time of the image is output followed with calculating the difference of the reading time and a time delay to obtain a taking time of the image. Finally, calculating the coordinate transformation of the calibrator coordinate and the operation target coordinate, and corresponding it to the image to output an image-coordinate correspondence relation. The time delay can be obtained correctly with only one test, and provided for the consequent synchronization calibration.

11 Claims, 6 Drawing Sheets

TIME SYNCHRONIZATION CALIBRATION METHOD AND SYSTEM FOR IMAGE TAKING AND COORDINATE READING AND DELAY TIME CALCULATION METHOD THEREOF

BACKGROUND OF THE INVENTION

1. Technical Field

The present invention relates to a calibration method and system, and a delay time calculation method thereof. More particularly, the present invention relates to a method and system for calibrating time synchronization between image taking and coordinate reading, and a delay time calculation method thereof, which are applied in the surgical navigation.

2. Description of Related Art

FIG. 1 shows an existing hardware arrangement for surgical navigation. In the surgical navigation hardware arrangement 10 of FIG. 1, dynamic reference frames (DRFs) 14a, 14b, and 14c are respectively provided on a surgical instrument 11, at a surgical site 12, and on a calibrator 13 mounted at the receiving end of an image taking device 17. Signals transmitted from an optical positioning device 15 are reflected by the DRFs 14a, 14b, and 14c and received by the optical positioning device 15. The surgical navigation system 16 receives the DRF coordinates of the calibrator 13 and of the surgical site 12 from the optical positioning device 15. Accompanying with the image of the calibrator 13 and the surgical site 12 taken by the image taking device 17 and the DRF coordinates, the surgical navigation system 16 calculates the relationship between the DRF coordinates and the image coordinates. Finally, the surgical site 12 and the dynamic position of the surgical instrument 11 can be displayed at the corresponding positions in the image to provide surgeons the desired surgical navigation information.

The surgical navigation system 16 depends heavily on a precise coordinate correspondence relationship. That is to say, the DRF coordinates must correspond precisely to the image coordinates, or the navigation information provided by the surgical navigation system 16 will be imprecise. However, even if the coordinates of the DRFs 14a, 14b, and 14c detected by the optical positioning device 15 are received by the surgical navigation system 16 immediately after the image taken by the image taking device 17 is received, there is always a time difference between the taking of the image and the reading of the DRF coordinates. Should the patient being operated on move during such a time difference, the DRF coordinates obtained will not correspond correctly to the image received; as a result, the navigation information becomes imprecise. Therefore, a method and system for calibrating the time difference between image taking and DRF coordinate reading is needed. It is desirable that the time difference only has to be calculated once for the same surgical navigation hardware arrangement 10 and can be used in all subsequent surgical navigation calibrations. It is also desirable that the surgical navigation system 16 is readily applicable to different surgical navigation hardware arrangements 10.

SUMMARY OF THE INVENTION

The present invention discloses a time synchronization calibration method and system for image taking and coordinate reading, and a delay time calculation method thereof. The calibration method includes: obtaining the coordinates of a calibrator and the coordinates of an operation target of each time point; reading the image of each time point; calculating the similarity index of each image; outputting an image reading time; calculating an image taking time; and outputting an image-coordinate correspondence relationship. The present invention allows a correct delay time to be obtained with only one test, and, once obtained, the delay time is applicable to all subsequent surgical navigation time compensations.

The present invention provides a time synchronization calibration method for image taking and coordinate reading, to be implemented in a computer system, the calibration method comprising the steps of: obtaining calibrator coordinates and operation target coordinates of each time point and storing the calibrator coordinates and the operation target coordinates of each said time point into a memory unit; reading an image of each said time point, wherein each said image is output by an X-ray instrument; calculating a similarity index of each said image, wherein a processing unit performs a similarity comparison between each said image and the image of an immediately preceding said time point to produce a said similarity index; outputting an image reading time, wherein when the similarity index of a said image with respect to the image of an immediately preceding said time point is lower than a preset similarity index, a time at which the image having the similarity index lower than the preset similarity index is read and output as the image reading time; calculating an image taking time, wherein the image taking time of the image corresponding to the image reading time is calculated by subtracting a delay time from the image reading time; and outputting an image-coordinate correspondence relationship, wherein a coordinate transformation calculation is performed on the calibrator coordinates and the operation target coordinates of the image taking time to obtain a corresponding coordinate relationship, and the coordinate relationship is related to the image corresponding to the image reading time to obtain the image-coordinate correspondence relationship for output.

The present invention also provides a time synchronization calibration system for image taking and coordinate reading, to be implemented in a computer system, the calibration system comprising: a reading module for reading and storing into a memory unit, at each time point, calibrator coordinates, operation target coordinates, and an image output by an X-ray instrument; a comparison module for reading the images in the memory unit, performing a similarity comparison between each said image and the image of an immediately preceding said time point through a processing unit, and outputting a similarity index of each said image as a comparison result; an output module for, when the similarity index of a said image is lower than a preset similarity index, obtaining an image reading time of the image from the memory unit and outputting the image reading time; a calculation module for calculating an image taking time of the image corresponding to the image reading time by subtracting a delay time from the image reading time; and an image-coordinate correspondence relationship output module for obtaining from the memory unit the calibrator coordinates and the operation target coordinates corresponding to the image taking time; performing a coordinate transformation calculation on the calibrator coordinates and the operation target coordinates obtained, so as to produce a coordinate transformation relationship; relating the coordinate transformation relationship to the image corresponding to the image reading time; and outputting an image-coordinate correspondence relationship.

The present invention further provides a delay time calculation method for use in time synchronization between image taking and coordinate reading, comprising the steps of: obtaining a first time, wherein a time at which a sensor senses an X ray generated by an X-ray instrument is read as the first time; reading a test image of each test time point and recording a time at which each said test image is read as a second time, wherein each said test image is output by the X-ray instrument; and calculating a delay time, wherein when a similarity index of a said test image with respect to the test image of an immediately preceding said test time point is lower than a preset similarity index, a difference between the first time and the second time of the test image having the similarity index lower than the preset similarity index is calculated as the delay time.

Implementation of the present invention at least produces the following advantageous effects:

1. The image taking time and the coordinate reading time can be calibrated synchronously.

2. The delay time only has to be measured once, and the measured delay time can be used in subsequent surgical navigation.

3. Universal applicability to different surgical navigation hardware arrangements is provided.

The detailed features and advantages of the present invention will be described in detail with reference to the preferred embodiment so as to enable persons skilled in the art to gain insight into the technical disclosure of the present invention, implement the present invention accordingly, and readily understand the objectives and advantages of the present invention by perusal of the contents disclosed in the specification, the claims, and the accompanying drawings.

BRIEF DESCRIPTION OF THE SEVERAL
VIEWS OF THE DRAWINGS

Figure 5:
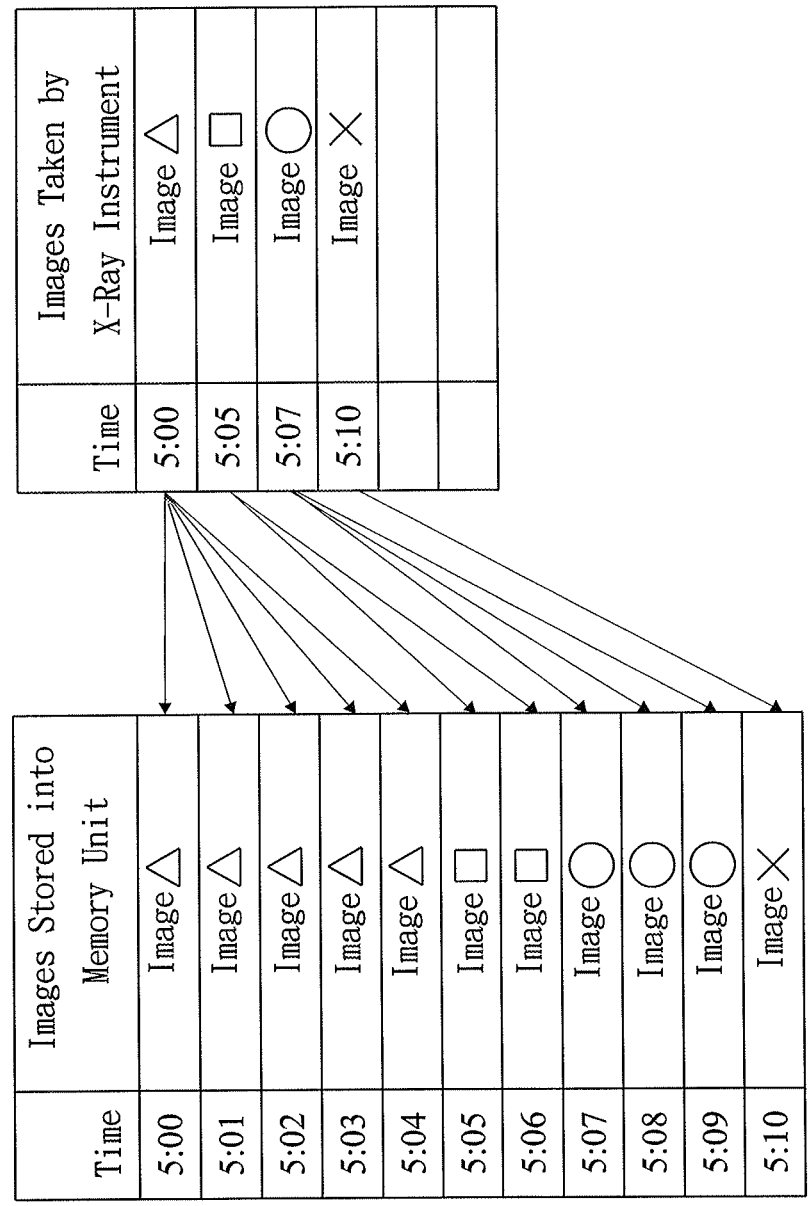
Figure 6:
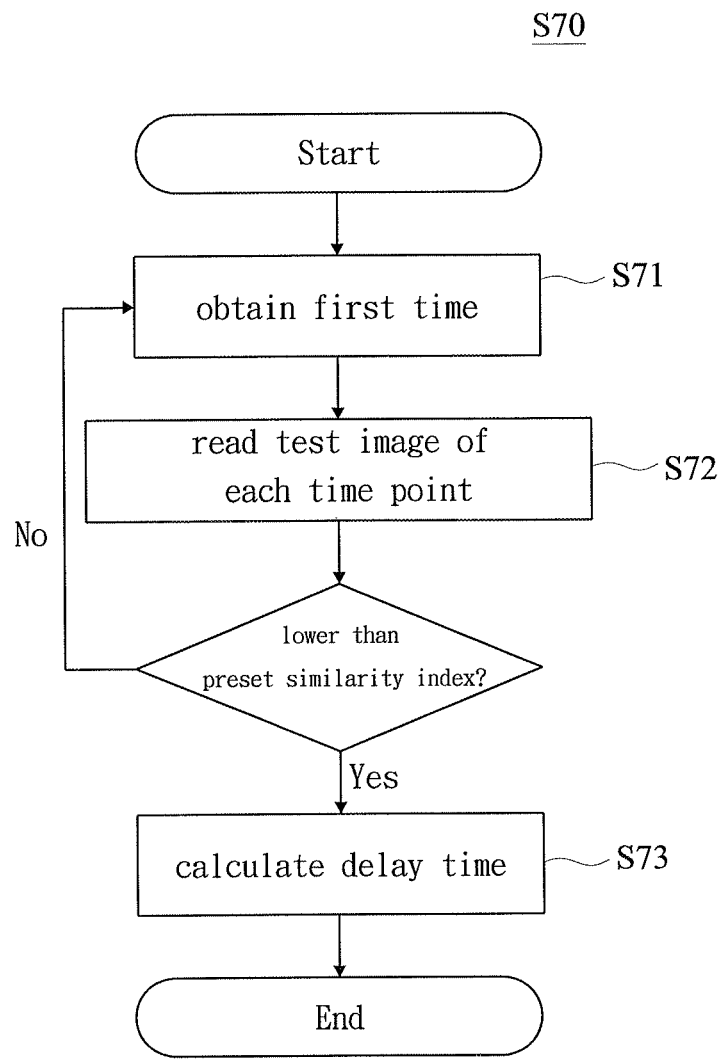

FIG. 5 schematically shows how the image of each time point is read according to an embodiment of the present invention; and FIG. 6 is the flowchart of a time difference calculation step in an embodiment of the present invention.

DETAILED DESCRIPTION OF THE
EMBODIMENTS OF THE INVENTION

Figure 1:
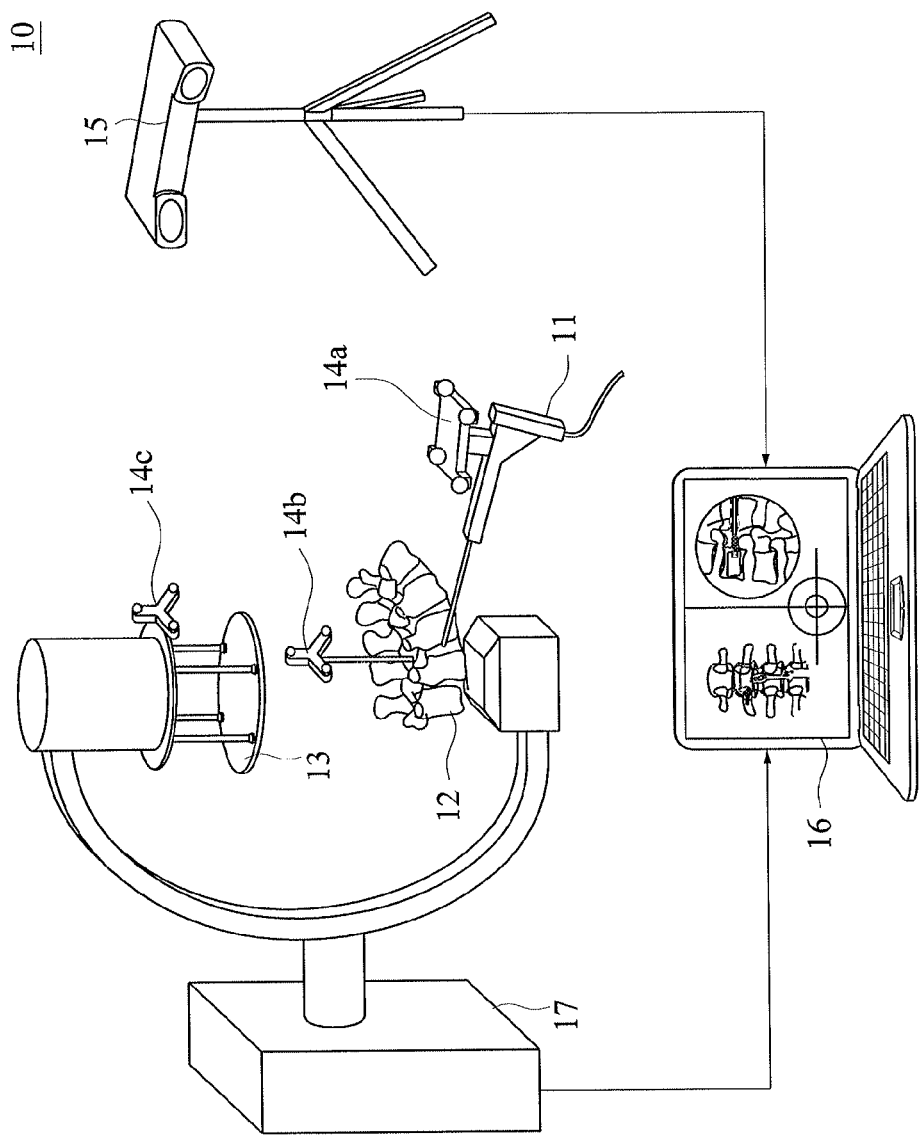
FIG. 1 shows an existing surgical navigation hardware arrangement.
Figure 2:
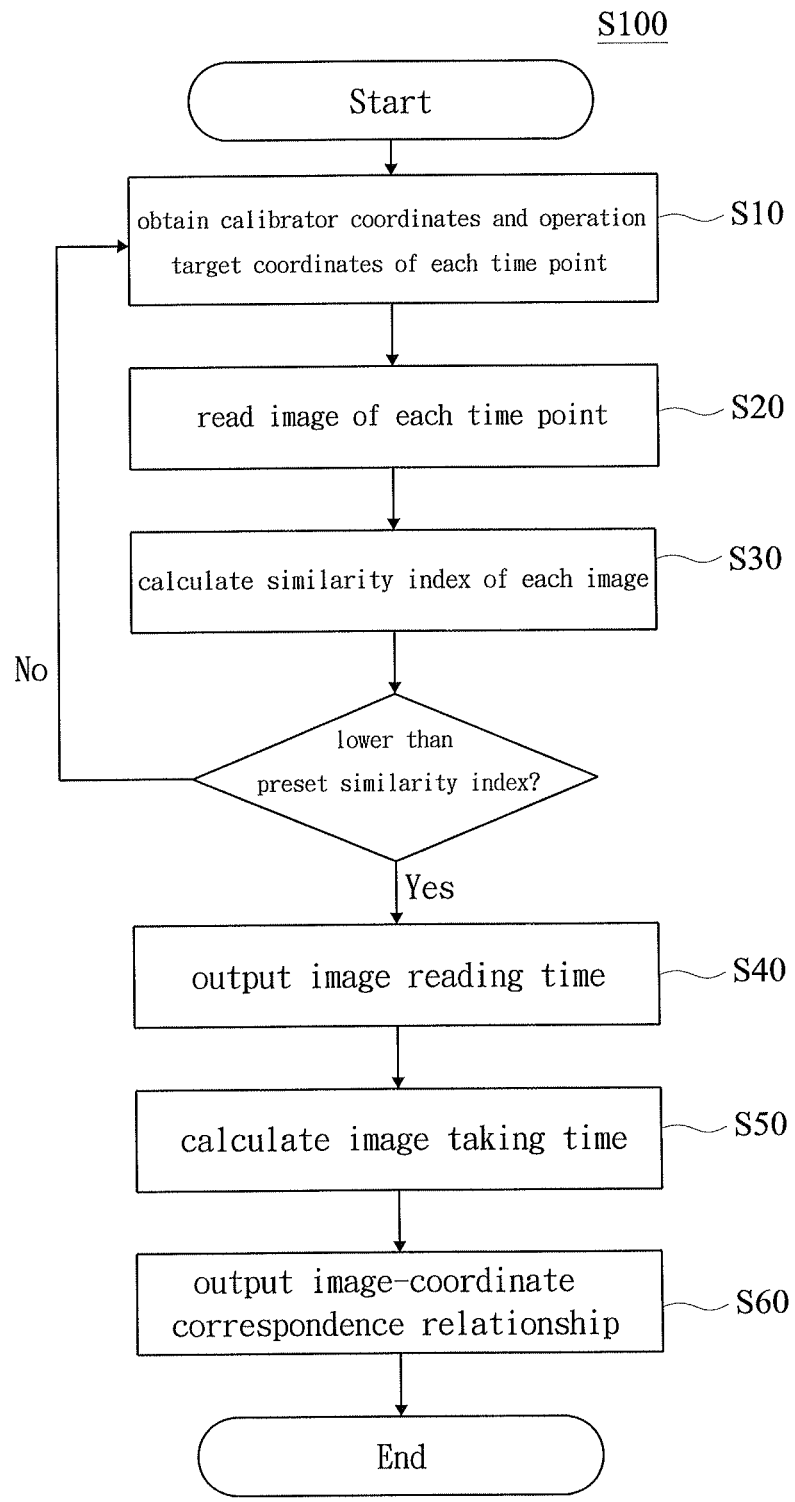
FIG. 2 is the flowchart of a time synchronization calibration method for image taking and coordinate reading according to an embodiment of the present invention.
Figure 3:
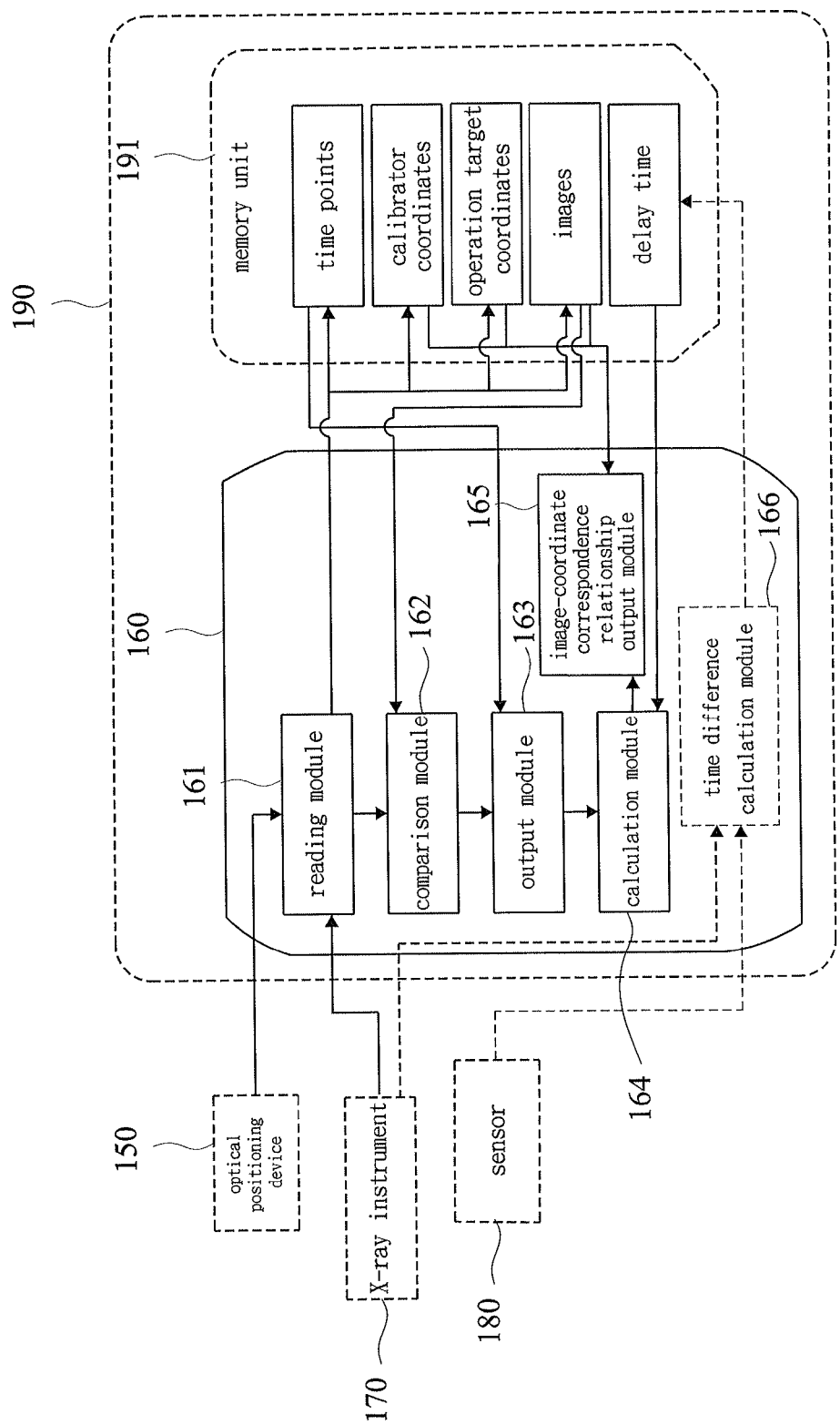
FIG. 3 is a block diagram of a time synchronization calibration system for image taking and coordinate reading according to an embodiment of the present invention.

FIG. 2 and FIG. 3 respectively show a time synchronization calibration method S100 and system 160 for image taking and coordinate reading according to an embodiment of the present invention. The calibration method S100 and system 160 are implemented in a computer system 190 which includes a memory unit 191 and a processing unit. The time synchronization calibration method S100 includes the steps of: obtaining the coordinates of a calibrator and the coordinates of an operation target of each time point (step S10); reading the image of each time point (step S20); calculating the similarity index of each image (step S30); outputting an image reading time (step S40); calculating an image taking time (step S50); and outputting an image-coordinate correspondence relationship (step S60). The time synchronization calibration system 160 for image taking and coordinate reading includes: a reading module 161, a comparison module 162, an output module 163, a calculation module 164, and an image-coordinate correspondence relationship output module 165.

Figure 4:
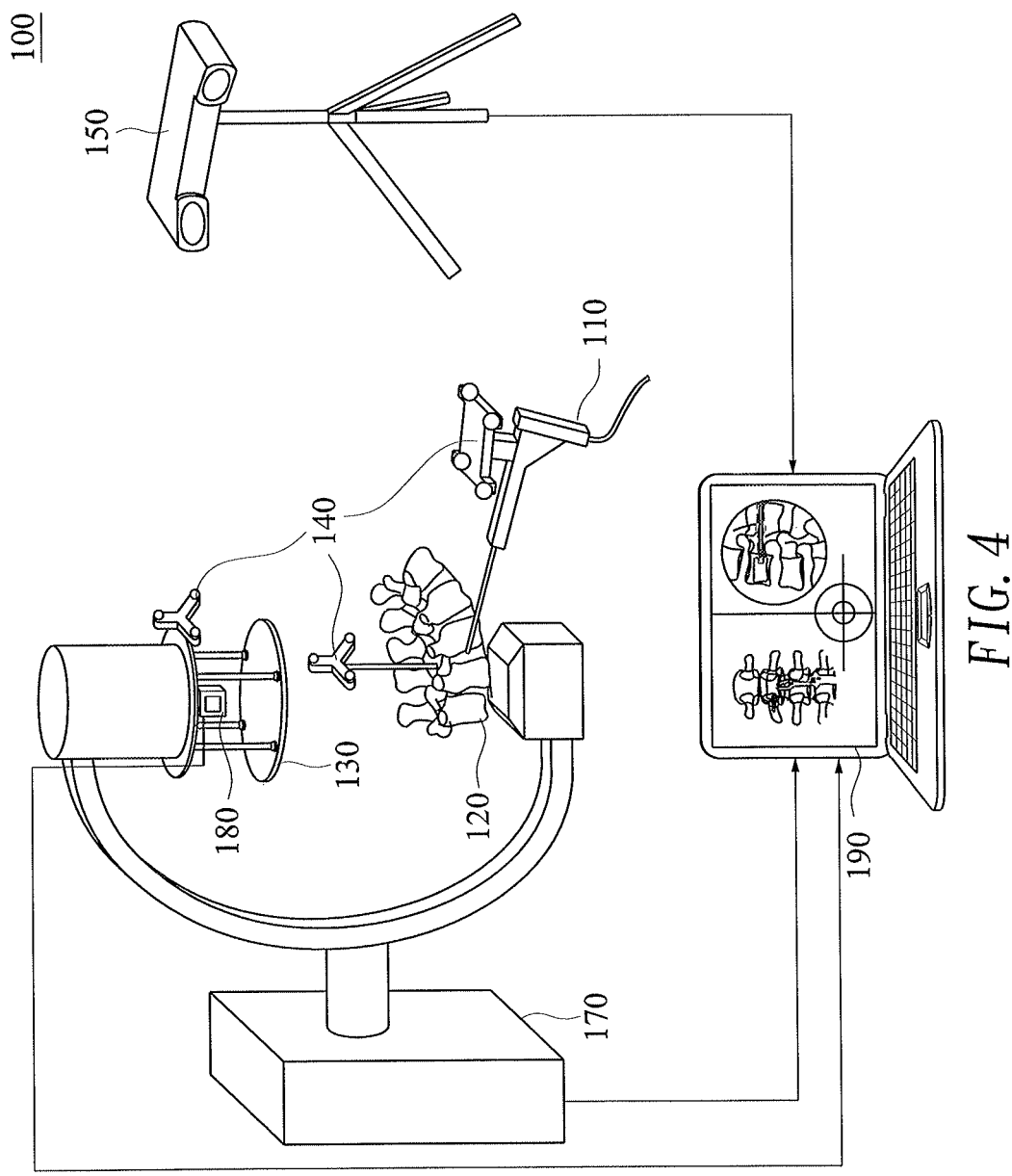
FIG. 4 shows a surgical navigation hardware arrangement according to an embodiment of the present invention.

The step of obtaining the coordinates of a calibrator and the coordinates of an operation target of each time point (step S10) is performed as follows. During surgical navigation, referring also to FIG. 4, the optical positioning device 150 receives the signals reflected by the DRFs 140, and the calibration system 160 reads from the optical positioning device 150 the coordinates of the calibrator 130 (hereinafter referred to as the calibrator coordinates) and the coordinates of the operation target 120 (hereinafter referred to as the operation target coordinates) of each time point by way of the reading module 161, wherein both the calibrator coordinates and the operation target coordinates use the DRF coordinate systems. The calibration system 160 stores each time point and the corresponding calibrator coordinates and operation target coordinates into the memory unit 191 of the computer system 190 to facilitate retrieval and use in the subsequent steps.

The step of reading the image of each time point (step S20) is now described with reference also to FIG. 5. During surgical navigation, a surgeon uses an X-ray instrument 170 to take images of the site to be operated on. The image output from the output port of the X-ray instrument 170 at each time point is read by the reading module 161 through the processing unit and is saved into the memory unit 191. The X-ray instrument 170 may be a C-arm fluoroscope.

Assume the X-ray instrument 170 takes an image Δ at 5:00, an image □ at 5:05, and an image ○ at 5:07. Therefore, at each time point ranging from 5:00 to 5:04, the image output from the X-ray instrument 170 is, as read by the reading module 161, the image Δ. Similarly, at 5:05 and 5:06, the image output from the X-ray instrument 170 as read by the reading module 161 is the image □.

To calculate the similarity index of each image (step S30), the comparison module 162 reads the images stored in the memory unit 191 and, by means of a processing unit, performs a similarity comparison between the image of the current time point and the image of the previous time point, before outputting the similarity index of the image of the current time point as the comparison result. Assume the current time point is 5:05. With the image of the current time point being the image □ and the image of the previous time point (i.e., 5:04) being the image Δ, the processing unit compares the image □ with the image Δ for similarity and outputs a similarity index. It should be pointed out that the interval between the time points is determined by the system designer or the user. In the present embodiment, the interval between the time points is one minute.

The similarity comparison, i.e., the calculation of the similarity index, is a normalized correlation coefficient (NCC) method, in which a correlation coefficient is calculated using the concept of dot product. The closer the correlation coefficient is to 1, the higher the similarity will be. The similarity index can be expressed by Euclidean distance, city block distance, Chebyshev distance, Mahalanobis distance, or chord distance.

The step of outputting an image reading time (step S40) is detailed as follows. If the similarity index of the image of a certain time point with respect to the image of the previous time point taken from the same angle is higher than a preset similarity index, meaning the images are substantially the same (i.e., the surgeon has not taken a new image), steps S10, S20, and S30 will be repeated for the next time point. If the similarity comparison result shows that the similarity index of the image of a certain time point with respect to the image of the previous time point taken from the same angle is lower than a preset similarity index (e.g., 0.8), meaning the surgeon has just taken a new image using the X-ray instrument 170, then a new image-coordinate correspondence relationship has to be established.

For example, at 5:04, the current image is the image Δ, which is the same as the image of 5:00, so the same image-coordinate correspondence relationship as at 5:00 applies. At 5:05, the surgeon takes the new image □, which is determined as different from the image Δ by the calibration system 160 through similarity comparison. Therefore, the image-coordinate correspondence relationship at 5:00 is no longer applicable. The calibration system 160 must obtain the image-coordinate correspondence relationship corresponding to the image □ in order to provide proper surgical navigation, as explained in further detail below. To begin with, the output module 163 obtains from the memory unit 191 the time point at which the reading module 161 reads the current image and, taking this time point as the image reading time, outputs the image reading time.

Following that, the step of calculating an image taking time (step S50) is performed. More specifically, the calculation module 164, after receiving the image reading time output from the output module 163 and a delay time stored in the memory unit 191, subtracts the delay time from the image reading time to obtain the correct image taking time of the image corresponding to the image reading time. The delay time is the time difference between the time at which the image is taken and the time at which the image is read by the calibration system 160. Hence, it can be known from step S50 at which time point the image read by the reading module 161 is taken by the X-ray instrument 170. The delay time may be stored in the memory unit 191.

Next, the step of outputting an image-coordinate correspondence relationship (step S60) is carried out. Now that a new image has been taken, a new image-coordinate correspondence relationship must be used. To obtain the new image-coordinate correspondence relationship, the image-coordinate correspondence relationship output module 165 obtains the image taking time calculated by the calculation module 164, retrieves from the memory unit 191 the calibrator coordinates and operation target coordinates corresponding to the image taking time, and performs a coordinate transformation calculation on the calibrator coordinates and operation target coordinates of the image taking time to obtain the corresponding coordinate transformation relationship, which may be a matrix transformation relationship. Then, the coordinate transformation relationship is related to the image corresponding to the image reading time to produce an image-coordinate correspondence relationship, which is output for use in subsequent surgical navigation, allowing the operation target 120 and the position of the surgical instrument 110 to be correctly displayed in the image. Only when the image is updated again (i.e., with the similarity index being lower than the preset similarity index again) will it be necessary to calculate a new image-coordinate correspondence relationship.

Referring to FIG. 6, the calibration method S100 further includes a time difference calculation step (step S70) for calculating the delay time. The time difference calculation step (step S70), performed by a time difference calculation module 166 further provided in the calibration system 160, includes the steps of: obtaining a first time (step S71), reading the test image of each test time point (step S72), and calculating the delay time (step S73).

Obtaining a first time (step S71): The X-ray instrument 170 must generate an X ray when taking a test image. Therefore, the time at which the X-ray instrument 170 generates the X ray is the correct image taking time of the test image. In order to obtain the image taking time of the test image, the time difference calculation module 166 reads the time at which the X-ray instrument 170 generates the X-ray, as sensed by a sensor 180, and takes this time as a first time.

Reading the test image of each test time point (step S72): Once the test image is taken, the time at which the test image is read is unobtainable because of the time difference between the time at which the test image is read and the actual image taking time. The time difference calculation module 166 therefore reads, at each test time point, the test image output from the X-ray instrument 170 and records the time at which each test image is read as a second time.

Calculating the delay time (step S73): If the test image of a certain test time point is determined, by means of a similarity comparison, to be highly similar to the test image of the previous test time point, meaning the test images are substantially the same (i.e., the X-ray instrument 170 has not taken a new test image), the test image of the next test time point will be read and compared with its immediate predecessor for similarity. If the similarity index of a test image with respect to the test image of the previous test time point is lower than a preset similarity index, meaning the X-ray instrument 170 has taken a new test image, the time at which this test image is read is the second time.

The time difference calculation module 166 calculates, via the processing unit, the difference between the first time, at which the sensor 180 detects an X ray, and the second time, at which the test image taken with this X ray is read, and stores the difference into the memory unit 191 as the delay time. The interval between the test time points is the same as that applied to the calibration system 160, and so is the preset similarity index stated in the previous paragraph. As a time difference is bound to occur between the taking of a test image and the reading of the test image, the time difference between the image reading time and the actual image taking time of the test image is the delay time used in the calibration method S100.

The delay time may be calculated separately in advance by a delay time calculation method for use in synchronizing image taking and coordinate reading. This delay time calculation method is identical to step S70. The delay time obtained is stored into the memory unit 191 and is applicable to subsequent surgical navigation calibrations. As the delay time caused by transmission between hardware components in the same surgical navigation hardware arrangement 100 is a constant, it is feasible to calculate the delay time only once for the same surgical navigation hardware arrangement 100; thus, the time required for calibration is significantly reduced. The calibration system 160 of the foregoing embodiment can also be used in other surgical navigation hardware arrangements 100 to increase the precision thereof.

The features of the present invention are disclosed above by the preferred embodiment to allow persons skilled in the art to gain insight into the contents of the present invention and implement the present invention accordingly. The preferred embodiment of the present invention should not be interpreted as restrictive of the scope of the present invention. Hence, all equivalent modifications or amendments made to the aforesaid embodiment should fall within the scope of the appended claims.

What is claimed is:

1. A time synchronization calibration method for image taking and coordinate reading, to be implemented in a computer system, the calibration method comprising the steps of:
   obtaining calibrator coordinates and operation target coordinates of each time point and storing the calibrator coordinates and the operation target coordinates of each said time point into a memory unit;

reading an image of each said time point, wherein each said image is output by an X-ray instrument;

calculating a similarity index of each said image, wherein a processing unit performs a similarity comparison between each said image and the image of an immediately preceding said time point to produce a said similarity index;

outputting an image reading time, wherein when the similarity index of a said image with respect to the image of an immediately preceding said time point is lower than a preset similarity index, a time at which the image having the similarity index lower than the preset similarity index is read is output as the image reading time;

calculating an image taking time, wherein the image taking time of the image corresponding to the image reading time is calculated by subtracting a delay time from the image reading time; and outputting an image-coordinate correspondence relationship, wherein a coordinate transformation calculation is performed on the calibrator coordinates and the operation target coordinates of the image taking time to obtain a corresponding coordinate relationship, and the coordinate relationship is related to the image corresponding to the image reading time to obtain the image-coordinate correspondence relationship for output.

2. The calibration method of claim 1, further comprising a time difference calculation step for calculating the delay time, wherein the time difference calculation step comprises the steps of:

obtaining a first time, wherein a time at which a sensor senses an X ray is read as the first time;

reading a test image of each test time point and recording a time at which each said test image is read as a second time, wherein each said test image is output by the X-ray instrument; and calculating the delay time, wherein when the similarity index of a said test image with respect to the test image of an immediately preceding said test time point is lower than the preset similarity index, a difference between the first time and the second time of the test images having the similarity index lower than the preset similarity index is calculated as the delay time.

3. The calibration method of claim 1, wherein the memory unit stores the delay time.

4. The calibration method of claim 1, wherein the similarity comparison is a normalized correlation coefficient (NCC) method.

5. The calibration method of claim 1, wherein the X-ray instrument is a C-arm fluoroscope.

6. A time synchronization calibration system for image taking and coordinate reading, to be implemented in a computer system, the calibration system comprising:

a reading module for reading and storing into a memory unit, at each time point, calibrator coordinates, operation target coordinates, and an image output by an X-ray instrument;

a comparison module for reading the images in the memory unit, performing a similarity comparison between each said image and the image of an immediately preceding said time point through a processing unit, and outputting a similarity index of each said image as a comparison result;

an output module for, when the similarity index of a said image is lower than a preset similarity index, obtaining an image reading time of the image from the memory unit and outputting the image reading time;

a calculation module for calculating an image taking time of the image corresponding to the image reading time by subtracting a delay time from the image reading time; and an image-coordinate correspondence relationship output module for obtaining from the memory unit the calibrator coordinates and the operation target coordinates corresponding to the image taking time; performing a coordinate transformation calculation on the calibrator coordinates and the operation target coordinates obtained, so as to produce a coordinate transformation relationship; relating the coordinate transformation relationship to the image corresponding to the image reading time; and outputting an image-coordinate correspondence relationship.

7. The calibration system of claim 6, further comprising a time difference calculation module for reading a test image output by the X-ray instrument and calculating through the processing unit a difference between a first time at which a sensor detects an X ray and a second time at which the test image is read, so as to obtain the delay time.

8. The calibration system of claim 6, wherein the memory unit stores the delay time.

9. The calibration system of claim 6, wherein the similarity comparison is a normalized correlation coefficient (NCC) method.

10. The calibration system of claim 6, wherein the X-ray instrument is a C-arm fluoroscope.

11. A delay time calculation method for use in time synchronization between image taking and coordinate reading, comprising the steps of:

obtaining a first time, wherein a time at which a sensor senses an X ray generated by an X-ray instrument is read as the first time;

reading a test image of each test time point and recording a time at which each said test image is read as a second time, wherein each said test image is output by the X-ray instrument; and calculating a delay time, wherein when a similarity index of a said test image with respect to the test image of an immediately preceding said test time point is lower than a preset similarity index, a difference between the first time and the second time of the test image having the similarity index lower than the preset similarity index is calculated as the delay time.

* * * * *